United States Patent
Xu et al.

(10) Patent No.: US 7,902,376 B2
(45) Date of Patent: Mar. 8, 2011

(54) PROCESS FOR PREPARING CHIRAL DIPEPTIDYL PEPTIDASE-IV INHIBITOR INTERMEDIATES

(75) Inventors: Feng Xu, Staten Island, NY (US); Mary M. Kim, Cheltenham, PA (US); Yoshinori Kohmura, Ibaraki (JP); Tricia Sladicka, Schenectady, NY (US); Jonathan D. Rosen, Iowa City, IA (US); Michael J. Zacuto, Jersey City, NJ (US)

(73) Assignees: Merck Sharp & Dohme Corp., Rahway, NJ (US); Banyu Pharmaceutical Co., Ltd., Tokyo (JP)

( * ) Notice: Subject to any disclaimer, the term of this patent is extended or adjusted under 35 U.S.C. 154(b) by 170 days.

(21) Appl. No.: 12/321,533

(22) Filed: Jan. 22, 2009

(65) Prior Publication Data
US 2009/0187028 A1    Jul. 23, 2009

Related U.S. Application Data

(60) Provisional application No. 61/062,058, filed on Jan. 23, 2008.

(51) Int. Cl.
*C07D 498/04*    (2006.01)
*C07D 487/04*    (2006.01)
*C07D 309/10*    (2006.01)

(52) U.S. Cl. ............ 548/218; 548/242; 548/360.5; 549/419

(58) Field of Classification Search .......... None
See application file for complete search history.

(56) References Cited

U.S. PATENT DOCUMENTS
2007/0232676 A1    10/2007    Biftu et al.

FOREIGN PATENT DOCUMENTS
WO    WO 2007/126745 A2    11/2007
WO    WO 2007/126745 A2 *    11/2007
WO    WO 2007/126745 A3    11/2007

* cited by examiner

*Primary Examiner* — Rebecca L Anderson
*Assistant Examiner* — Alicia L Otton
(74) *Attorney, Agent, or Firm* — Janet E. Fair; John C. Todaro

(57) ABSTRACT

A novel process is provided for the preparation of chiral trans-2,3-disubstituted 5-oxotetrahydropyrans of structural formula (I):

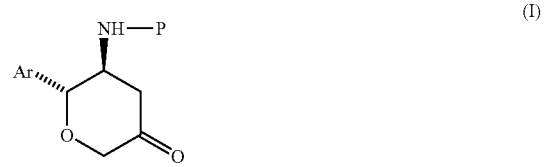

wherein Ar is optionally substituted phenyl and P is a primary amine protecting group. These compounds are useful in the synthesis of dipeptidyl peptidase-IV inhibitors for the treatment of Type 2 diabetes. Also provided are useful intermediates obtained from the process.

12 Claims, No Drawings

PROCESS FOR PREPARING CHIRAL DIPEPTIDYL PEPTIDASE-IV INHIBITOR INTERMEDIATES

CROSS-REFERENCE TO RELATED APPLICATIONS

The present invention is related to U.S. provisional application Ser. No. 61/062,058, filed Jan. 23, 2008, the contents of which are hereby incorporated by reference in their entirety.

FIELD OF THE INVENTION

The present invention discloses a novel process and novel intermediates toward the preparation of chiral trans-2,3-disubstituted 5-oxotetrahydropyrans which are useful as intermediates in the synthesis of dipeptidyl peptidase-IV (DPP-4) inhibitors for the treatment of Type 2 diabetes.

BACKGROUND OF THE INVENTION

The present invention provides an efficient process for the preparation of chiral trans-2,3-disubstituted 5-oxotetrahydropyrans of structural formula (I):

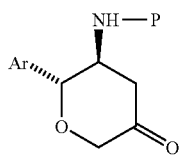

(I)

wherein Ar is phenyl optionally substituted with one to five $R^1$ substituents;
each $R^1$ is independently selected from the group consisting of:
   fluorine,
   chlorine,
   $C_{1-6}$ alkyl, optionally substituted with one to five fluorines, and
   $C_{1-6}$ alkoxy, optionally substituted with one to five fluorines;
and P is a primary amine protecting group.

The present invention also provides intermediates useful in the disclosed process.

The synthesis of tetrahydropyran-3-ones of structural formula (I) has previously been described in PCT international patent application WO 2007/126745, which published on Nov. 18, 2007. In this publication, the pyranone was elaborated in a racemic 10-step sequence involving heating a nitroketone with 3-iodo-2-(iodomethyl)prop-1-ene and further chemical manipulation. Resolution of the racemic product was achieved by chiral chromatography.

In the present invention, chiral intermediates of structural formula (I) are produced in an efficient enantioselective manner starting from a lower alkyl N-(diphenylmethylene)glycinate. The process involves a one-pot elaboration of a Weinreb amide, generation of an optionally substituted phenyl ketone, transfer hydrogenation of the ketone with installation of two stereogenic centers through a highly enantioselective ruthenium (Ru) metal-catalyzed dynamic kinetic resolution (DKR) asymmetric transfer hydrogenation, a rhodium (Rh)— or ruthenium-metal catalyzed cycloisomerization to construct the dihydropyran skeleton, hydroboration with oxidative work-up to generate a pyran-5-ol, and oxidation to afford the desired pyranone final product of formula (I).

SUMMARY OF THE INVENTION

This invention is concerned with a process for preparing chiral trans-2,3-disubstituted tetrahydropyran-5-ones of structural formula (I) and certain useful intermediates obtained during that process. The process features the generation of a protected propargylglycine Weinreb amide from a lower alkyl N-(diphenylmethylene)glycinate, a Grignard addition reaction to afford an optionally substituted phenyl ketone, a highly enantioselective Ru-catalyzed dynamic kinetic resolution (DKR) asymmetric transfer hydrogenation, a Rh- or Ru-catalyzed cycloisomerization to construct the dihydropyran nucleus, hydroboration with oxidative work-up to afford a pyranol, and final oxidation to provide the desired chiral tetrahydropyran-5-one final product.

As disclosed in WO 2007/126745, compounds of structural formula (I) represent key intermediates in the preparation of dipeptidyl peptidase-IV (DPP-4) inhibitors which are useful for the treatment of Type 2 diabetes. The DPP-4 inhibitors can be elaborated by reductive amination of the tetrahydropyran-5-ones and removal of the primary amine protecting group.

DETAILED DESCRIPTION OF THE INVENTION

The process of the present invention involves the preparation of a compound of structural formula (I):

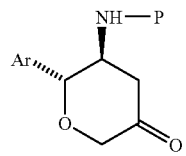

(I)

wherein Ar is phenyl optionally substituted with one to five $R^1$ substituents;
each $R^1$ is independently selected from the group consisting of:
   fluorine,
   chlorine,
   $C_{1-6}$ alkyl, optionally substituted with one to five fluorines, and
   $C_{1-6}$ alkoxy, optionally substituted with one to five fluorines;
and P represents a primary amine protecting group;
comprising the steps of:
(a) producing a compound of structural formula (II):

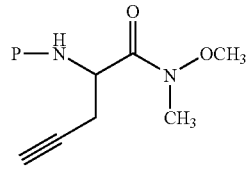

(II)

by (i) alkylating a $C_{1-6}$ alkyl N-(diphenylmethylene)glycinate with a propargyl sulfonate or propargyl halide in the presence of base followed by treatment with acid to liberate the free primary amine; (ii) reacting said liberated primary amine with a primary amine protecting reagent in the presence of base; and (iii) treating the resulting N-protected amino acid with N,O-dimethylhydroxylamine in the presence of an activating reagent in a suitable organic solvent;
(b) producing a compound of structural formula (III):

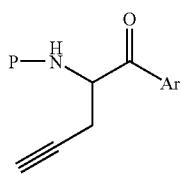
(III)

by treating a compound of structural formula (II) with a Grignard reagent of structural formula (IV):

ArMgBr or ArMgI         (IV)

in a suitable organic-solvent;
(c) producing a compound of structural formula (V):

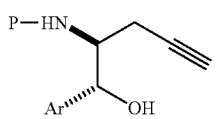
(V)

by treating a compound of structural formula (III) in a suitable organic solvent with a source of hydrogen, a base, and a Ru($\eta^6$-arene)-N-sulfonyl-1,2-diamine catalyst;
(d) producing a compound of structural formula (VI):

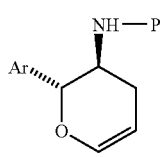
(VI)

by subjecting a compound of structural formula (V) to rhodium- or ruthenium-catalyzed cycloisomerization conditions in a suitable organic solvent;
(e) producing a compound of structural formula (VII):

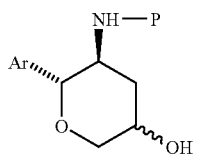
(VII)

by hydroboration of a compound of structural formula (VI) with a suitable borane reagent followed by oxidative work-up; and
(f) treating a compound of structural formula (VII) with a suitable oxidizing agent in a suitable solvent to afford a compound of structural formula (I).

In one embodiment of the process of the present invention, each $R^1$ is independently selected from the group consisting of fluorine, chlorine, methyl, trifluoromethyl, and trifluoromethoxy. In a class of this embodiment, Ar is 2,5-difluorophenyl or 2,4,5-trifluorophenyl. In a subclass of this class, Ar is 2,5-difluorophenyl.

In a second embodiment of the process of the present invention, the product of Step (e) of the reaction sequence is isolated from the reaction mixture which can be converted into the final DPP-4 inhibitor compounds of structural formula (VIII) disclosed in WO 2007/126745 as shown in the following Scheme:

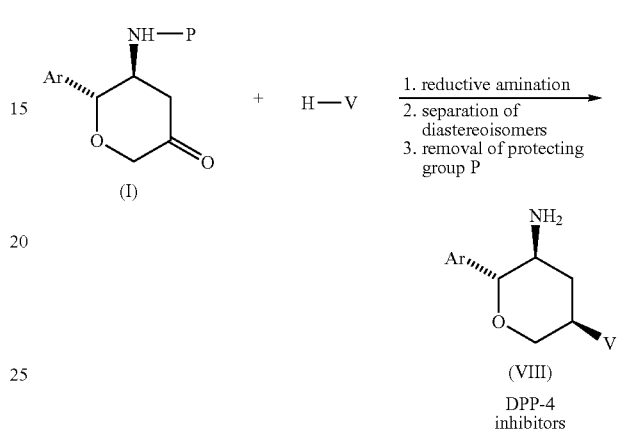

wherein V is selected from the group consisting of:

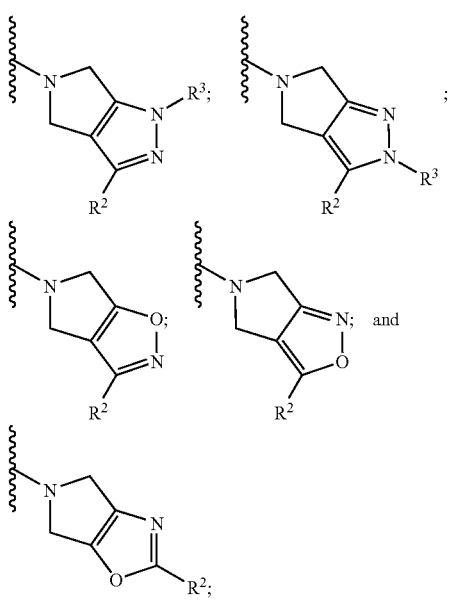

and $R^2$ and $R^3$ are each independently selected from the group consisting of hydrogen, $C_{1-3}$ alkyl, trifluoromethyl, 2,2,2-trifluoroethyl, and cyclopropyl. In a class of this embodiment, Ar is 2,5-difluorophenyl.

In a third embodiment of the process of the present invention, each process step can be carried out without the need for isolating the intermediates of structural formulae (II) to (VII).

The final product of formula (I) and the various intermediates in the process of the present invention can be isolated using techniques well-known in the art of synthetic organic chemistry including, but not limited to, crystallization, recrystallization, filtration, trituration, distillation, and chromatography, such as thin-layer chromatography, column chromatography on silica gel, and high-performance liquid chromatography (HPLC).

The first step in the process of the present invention is alkylation of a lower alkyl ($C_{1-6}$) N-(diphenylmethylene)glycinate (1) with a propargyl alkyl- or arylsulfonate or a propargyl halide, such as propargyl bromide, in the presence of a base and optionally a phase transfer catalyst such as tetra-n-butylammonium bromide ($Bu_4NBr$) in a suitable organic solvent which alkylation reaction is followed by an acidic workup to afford an amino ester in one-pot. Preferred lower alkyl glycinates are methyl and ethyl glycinate. Preferred propargyl arylsulfonates are propargyl benzenesulfonate (besylate) and propargyl p-toluenesulfonate (tosylate). A particularly suitable base for the alkylation step is cesium carbonate and a suitable solvent is methyl tert-butyl ether (MTBE). In one embodiment of this conversion, cesium carbonate is added to a mixture of the glycine imine, propargyl besylate, and $Bu_4NBr$ in MTBE. The alkylated product a is then treated with aqueous acid, such as aqueous hydrochloric acid (HCl), to generate the free amine which is then neutralized with aqueous base, such as aqueous sodium hydroxide (NaOH), and treated with a suitable primary amine protecting group (P) to afford c. Examples of suitable primary protecting groups include t-butyloxycarbonyl (Boc), benzyloxycarbonyl (Cbz), 9-fluorenylmethyl-oxycarbonyl (FMOC), acetyl, formyl, phthaloyl, benzoyl, and pivaloyl. One embodiment of the amine protecting group (P) is Boc which is removable under acidic conditions, such as aqueous HCl, aqueous sulfuric acid, and trifluoroacetic acid in an organic solvent. Conversion of the N-protected amino acid c to the Weinreb amide d is carried out by activation of the acid moiety in c with an activating reagent such as 1,1'-carbonyldiimidazole to generate an acyl imidazole and subsequent treatment with N,O-dimethylhydroxylamine (Weinreb amine) in a suitable solvent, such as N,N-dimethylformamide (DMF). The five chemical steps can be carried out in a through-process without isolating any of the intermediates. The Weinreb amide d can be purified by crystallization prior to further chemical transformation.

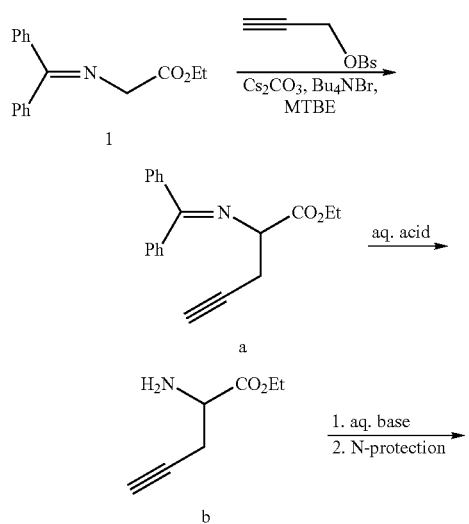

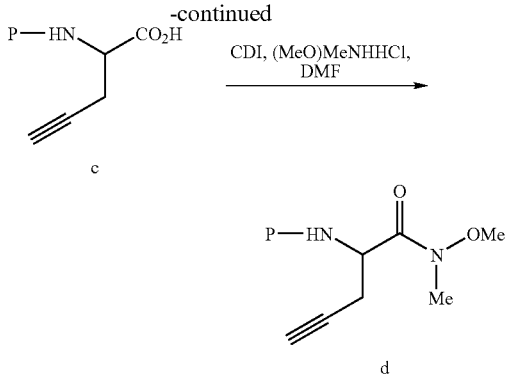

The next step of the process is addition of an optionally substituted phenyl Grignard reagent to the Weinreb amide d in a suitable organic solvent to generate an optionally substituted phenyl ketone e. This can be efficiently accomplished using two equivalents of an optionally substituted phenyl Grignard reagent generated in situ by treating an optionally substituted bromo- or iodobenzene with iPrMgCl or iPrMgCl/LiCl (Turbo Grignard) or, alternatively, using two equivalents of iPrMgCl, one to deprotonate the Weinreb amide and the other to generate the Grignard reagent from an optionally substituted bromo- or iodobenzene. Suitable organic solvents for this addition reaction include toluene, $CH_2Cl_2$, THF, and mixtures thereof.

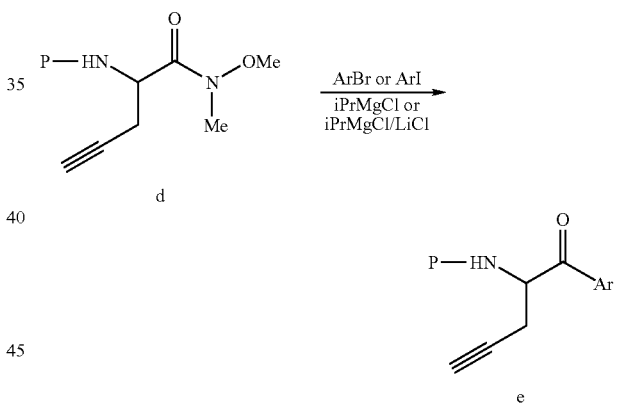

The next step in the process is a Ru(II)-catalyzed dynamic kinetic resolution (DKR) asymmetric transfer hydrogenation using a Ru($\eta^6$-arene)-N-sulfonyl-1,2-diamine catalyst and, in particular, a Ru(p-cymene)-N-sulfonyl-1,2-diphenylethylenediamine (DPEN) catalyst developed by Noyori [see R. Noyori, et al., *J. Org. Chem.*, 66: 7931-7944 (2001) and B. Mohar, et al., *Chem. Commun.*, 2572-2573 (2001)]. The reaction is performed in the presence of a hydrogen donor, such as formic acid, ammonium formate, and 2-propanol, and a base in a suitable organic solvent. Preferred bases include amine bases, such as $Et_3N$, DBU, DABCO, and morpholine. In one embodiment, the amine base is DABCO. The $\eta^6$-arene is benzene or p-cymene. The chiral N-sulfonyl-DPEN ligands include, but are not limited to, TsDPEN (N-tosyl-diphenylethylenediamine), FsDPEN(N-pentafluorophenylsulfonyl-diphenylethylenediamine), N-4-(trifluoromethyl)benzene-sulfonyl-diphenylethylenediamine, and N-trifluoromethylsulfonyl-diphenylethylenediamine. Suitable organic solvents include, but are not limited to, THF, MTBE, CH$_2$Cl$_2$, and mixtures thereof.

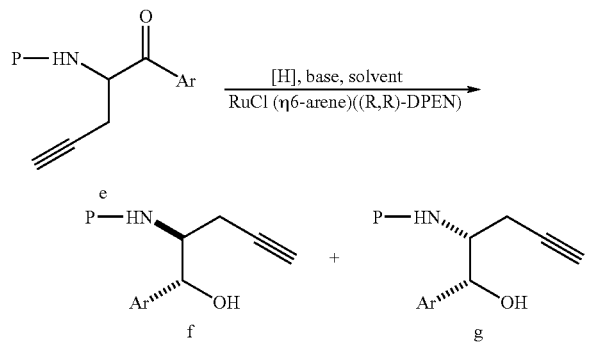

The DKR transfer hydrogenation proceeds with high chemical conversions and with a d.e. of the desired diastereoisomer f to the minor diastereoisomer g of about 75% and an e.e. of greater than 97%.

This asymmetric DKR transfer hydrogenation step is followed by a rhodium- or ruthenium-catalyzed cycloisomerization step to construct the dihydropyran skeleton. The rhodium-catalyzed method employs technology described by B. Trost et al., in *J. Amer. Chem. Soc.*, 125: 7482-7483 (2003). This transformation can be performed on diastereoisomer f or a mixture of diastereoisomers f and g obtained from the DKR-reduction step without isolating f. In one embodiment the rhodium catalyst is preformed by heating the phosphine ligand and rhodium trichloride hydrate in a suitable solvent, such as aqueous ethanol. Preferred phosphine ligands are triphenylphosphine, tris(3-fluorophenyl)phosphine, tris(3,5-difluorophenyl)phosphine, and tris(4-fluorophenyl)phosphine, and, in particular tris(3-fluorophenyl)phosphine. The reaction is performed in a suitable organic solvent, such as DMF, at elevated temperatures, such as about 60° C. to about 100° C.

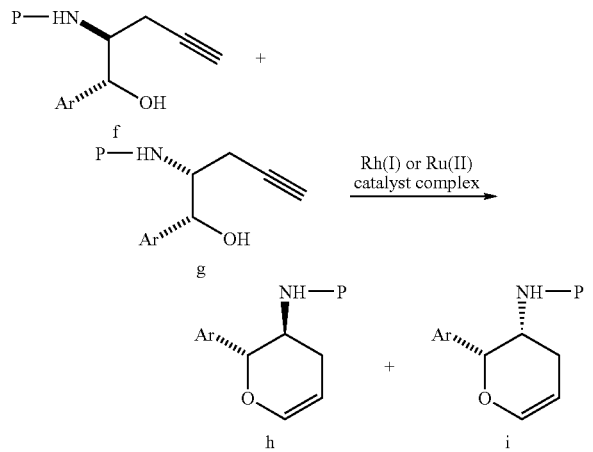

The ruthenium-catalyzed approach depicted in the Scheme below is a variant of the method described by B. Trost, et al., in *J. Amer. Chem. Soc.*, 124: 2528-2533 (2002) and entails treating diastereoisomer f or a mixture of diastereoisomers f and g obtained from the DKR-reduction step with a Ru catalyst in the presence of a mild oxidant, a base, a triarylphosphine ligand, and tetrabutylammonium hexafluorophosphate.

The Ru catalyst is preferably CpRuCl(Ar$_3$P)$_2$, the mild oxidant is preferably N-hydroxysuccinimide (NHS), and the base is preferably sodium hydrogencarbonate. Preferred triarylphosphine ligands are triphenylphosphine, tris(4-fluorophenyl)phosphine, tris(3-fluorophenyl)phosphine, tris(4-methoxyphenyl)phosphine, and tris(2-furyl)phosphine. In one embodiment, the Ru catalyst is CpRuCl(Ph$_3$P)$_2$ and the triarylphosphine ligand is triphenylphosphine. The reaction is carried out in suitable organic solvent, such as DMF or aqueous DMF at elevated temperatures, such as about 60° C. to about 100° C.

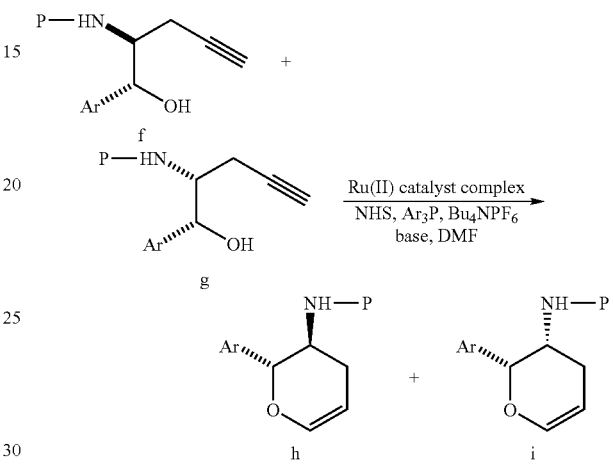

The cycloisomerization step is followed by hydroboration of the diastereo-isomeric mixture of h and i and subsequent oxidative work-up to generate the diastereo-isomeric mixture of pyranols j and k.

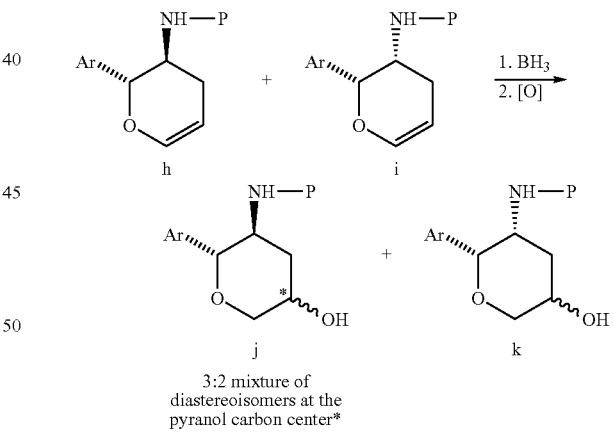

3:2 mixture of diastereoisomers at the pyranol carbon center*

The hydroboration of the dihydropyran mixture h and i is carried out with a borane reagent in a suitable organic solvent. Among the borane reagents suitable to effect this conversion are borane-dimethyl sulfide (BH$_3$—SMe$_2$), BH$_3$-THF, and 9-BBN. A preferred borane reagent is BH$_3$—SMe$_2$. The reaction is performed using an excess of the borane reagent relative to the dihydropyran substrate. Enhanced conversions are obtained using about 2 to about 5 equivalents of the borane reagent, and, in particular, about 2.5 equivalents. Suitable organic solvents for this hydroboration step include, but are not limited to, toluene, MTBE, THF, and mixtures thereof. The reaction is carried at temperatures of about −25° C. to about 50° C. The oxidative work-up uses a suitable oxidant, such as hydrogen peroxide and sodium perborate (NaBO$_3$) in aqueous base, such as aqueous sodium hydroxide and sodium hydrogencarbonate. In one embodiment the oxidant is sodium perborate tetrahydrate/NaOH. The desired pyranol j is obtained as a 3:2 mixture of diastereoisomers at the pyranol stereogenic carbon center designated with an *. Crystallization in a suitable organic solvent, such as a mixture of toluene and heptane, rejects the undesired diastereoisomeric mixture of pyranols k which remain in the mother liquor. Rejection of heavy metal Rh and Ru residues in the isolated product is facilitated by the introduction of tri-n-butylphosphine during the crystallization.

The final step in the process of the present invention is oxidation of the pyranol mixture j to give the desired tetrahydropyran-3-one m.

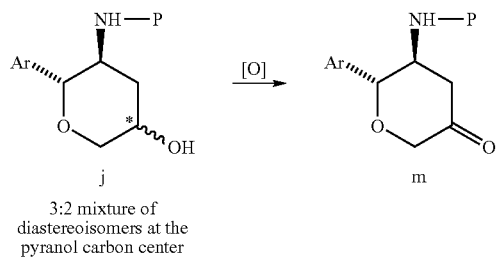

3:2 mixture of
diastereoisomers at the
pyranol carbon center

The oxidants that can be employed in the reaction include, but are not limited to, RuO$_2$—NaBrO$_3$, RuCl$_3$—NaClO$_3$, RuCl$_3$—NaBrO$_3$, TEMPO-NaBrO$_3$, Oxone, Oxone-acetone, Oxone-NaBr, and trichloroisocyanuric acid. In one embodiment, the oxidant is catalytic RuCl$_3$ and stoichiometric NaBrO$_3$. The oxidation is carried out in a suitable system such as buffered acetonitrile-acetic acid. The oxidation is carried out using conditions to minimize over-oxidation, such as running the reaction at about 0° C. and in a solvent such that the desired ketone m crystallizes from the reaction mixture. The crystallization is facilitated by the addition of water to the mixture.

Another aspect of the present invention is concerned with novel compounds of structural formulae (III), (V), (VI), and (VII) which are useful intermediates in the preparation of the compounds of structural formula (I):

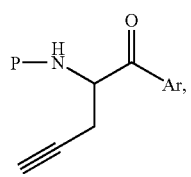

(III)

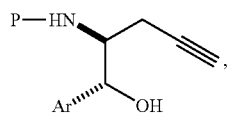

(V)

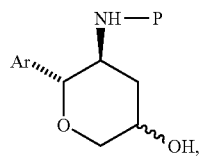

(VII)

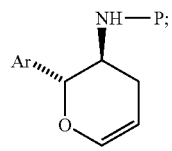

(VI)

wherein Ar is phenyl optionally substituted with one to five R$^1$ substituents;

each R$^1$ is independently selected from the group consisting of:
fluorine,
C$_{1-6}$ alkyl, optionally substituted with one to five fluorines, and C$_{1-6}$ alkoxy, optionally substituted with one to five fluorines; and P is selected from the group consisting of acetyl, formyl, benzoyl, pivaloyl, phthaloyl, t-butyloxycarbonyl, benzyloxycarbonyl, and 9-fluorenylmethyloxycarbonyl. In one embodiment of this aspect of the present invention, Ar is 2,5-difluorophenyl or 2,4,5-trifluorophenyl and P is t-butyloxycarbonyl (Boc).

Representative experimental procedures utilizing the novel process are described below. For purposes of illustration, the following Example is directed to the preparation of tert-butyl [(2R,3S)-2-(2,5-difluorophenyl)-5-oxotetrahydro-2H-pyran-3-yl]carbamate (9), but doing so is not intended to limit the process of the present invention to the specific conditions for making this particular compound.

Abbreviations:
AcOH=acetic acid
Ar=aryl
Boc=tert-butyloxycarbonyl
Bs=benzenesulfonyl
CDI=1,1'-carbonyldiimidazole
CH$_2$Cl$_2$ dichloromethane
Cp=cyclopentadienyl
Cs$_2$CO$_3$=cesium carbonate
d=day(s)
DABCO=1,4-diazabicyclo[2.2.2]octane
DBU=1,8-diazabicyclo[5.4.0]undec-7-ene
DMF=N,N-dimethylformamide
DMS=dimethylsulfide
Et=ethyl
h=hour(s)
HPLC=high-performance liquid chromatography
iPAc=isopropyl acetate
iPr=isopropyl
iPrOH=isopropyl alcohol or 2-propanol
L=liter(s)
MeCN=acetonitrile
Me=methyl
min minute(s)
mL=milliliter(s)
MTBE=methyl tert-butyl ether
Ph=phenyl
rt=room temperature
THF=tetrahydrofuran By halogen is meant fluorine, chlorine, bromine, or iodine.

The term "% enantiomeric excess" (abbreviated "e.e.") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

The term "% diastereoisomeric excess" (abbreviated "d.e.") shall mean the % major diastereoisomer less the % minor diastereoisomer. Thus, a 90% diastereoisomeric excess corresponds to formation of 95% of one diastereoisomer and 5% of the other.

Certain starting materials and reagents are either commercially available or known in the chemical scientific or patent literature. Purification procedures include, for example, distillation, crystallization, and normal or reverse phase high performance liquid chromatography.

Example 1

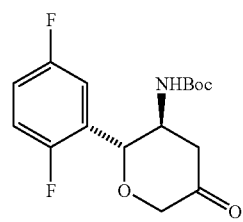

tert-Butyl [(2R,3S)-2-(2,5-difluorophenyl)-5-oxotetrahydro-2H-pyran-3-yl]carbamate

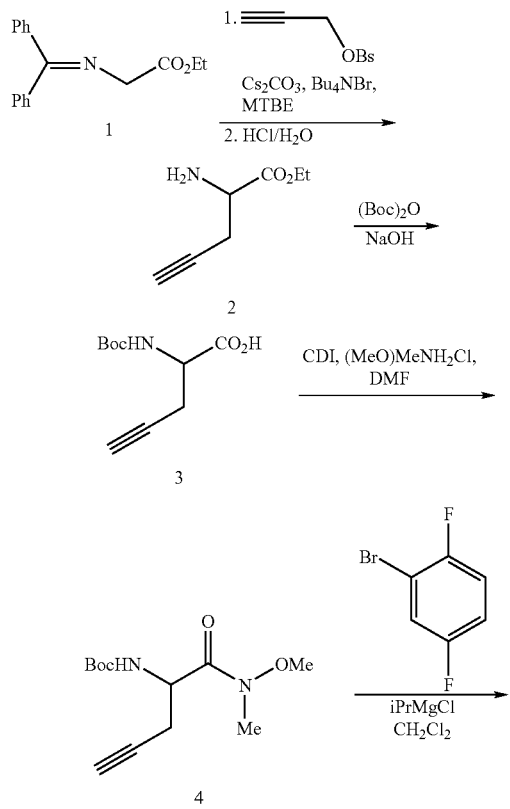

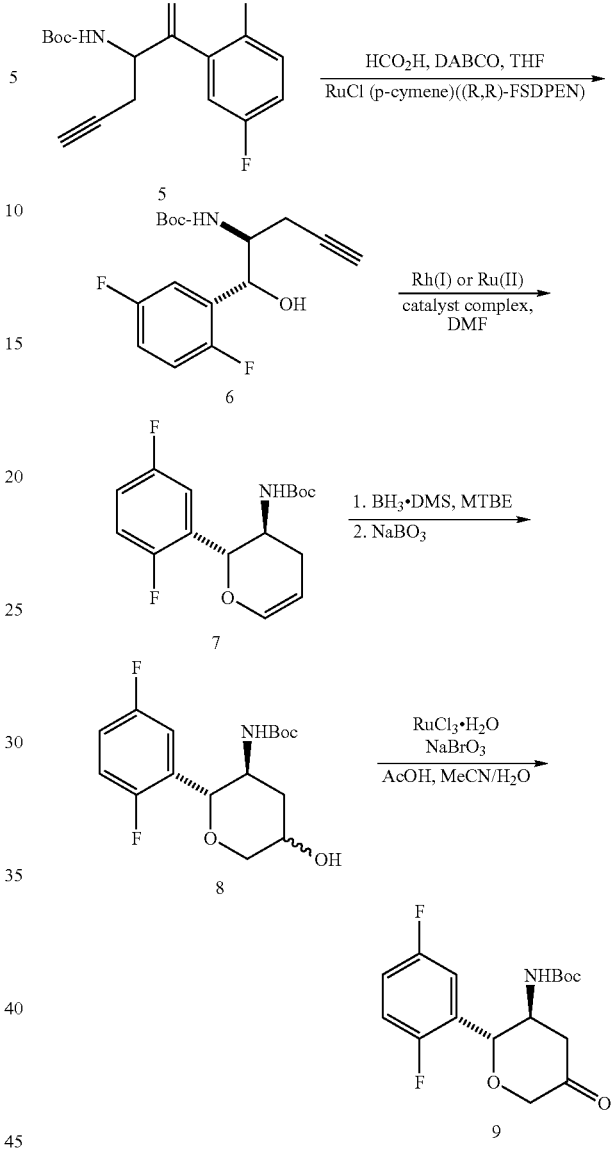

Step 1: Preparation of Weinreb Amide 4

(a) Alkylation of 1 with Propargyl Besylate

To a solution of ethyl N-(diphenylmethylene)glycinate (1) (100 g, 0.374 mol), propargyl besylate (70.9 mL, 0.449 mol), and Bu$_4$NBr (12.1 g, 37.4 mmol) in MTBE (1 L) at 50° C. was added Cs$_2$CO$_3$ (244 g, 0.748 mol). The resulting slurry was stirred at 50° C. until the ratio of the desired product to starting material was greater than 100 as determined by HPLC (typically overnight to 2 d). The slurry was then cooled to rt. The inorganic solids were filtered off and rinsed with MTBE (250 mL). The combined filtrate was directly used for the next step.

(b) Hydrolysis and Boc Protection to Provide 3:

A solution of the propargyl imine (114 g, 0.374 mol) in MTBE [from the alkylation step (a)] was concentrated to 500 mL. 1 N aqueous HCl (411 mL, 0.411 mol) was then added to the above solution dropwise at rt. After complete consumption of the imine as determined by HPLC of the organic layer, the organic layer was discarded. The aqueous layer was extracted with MTBE (100 mL). The small amount of insoluble precipitate was removed by filtration and washed with H$_2$O (100 mL). The combined aqueous layer was basified with 50 w/w % aqueous NaOH (ca. 18.75 N, 59.8 mL, 1.122 mol) and stirred for 0.5 h at rt. Water (65 m/L) was added followed by a solution of di-tert-butyl dicarbonate (Boc$_2$O) (89.8 g, 0.411 mol) in MTBE (250 mL) at rt. The resulting biphasic reaction mixture was stirred several hours. The organic layer was discarded. The aqueous layer was washed with MTBE (100 mL), acidified with 37% aqueous HCl to pH 3. MTBE (500 mL) was added to the aqueous layer. Another portion of 37% aqueous HCl was added to adjust to pH 3. The organic layer was then separated and the aqueous layer was extracted with MTBE (250 mL). The combined organic layer was assayed by HPLC, azeotropically dried with MTBE, and then solvent-switched to DMF (284 mL), which was used directly for the next step.

(c) Conversion to Weinreb Amide 4

A solution of acid 3 from step (b) (71.0 g, 0.333 mol) in DMF (284 µL) was added 1,1'-carbonyldiimidazole (70.2 g, 0.433 mol) in portions below 10° C. The resulting reaction mixture was stirred at 0° C. for several hours. N,O-Dimethylhydroxylamine HCl (39.0 g, 0.40 mol) was added in portions below 10° C. The resulting reaction mixture was stirred at rt until the ratio of Weinreb amide 4 to n-butyl amide was greater than 500 as determined by HPLC [a small amount of the reaction mixture was quenched in n-butylamine at rt and diluted with acetonitrile and water (about 1:1) to check the conversion]. Water (710 µL) was added dropwise over 2 h. The resulting slurry was aged overnight at rt, cooled to 0° C. gradually, and aged for 2 h at 0° C. The product was collected by filtration, washed with DMF/H$_2$O=⅛ (70 mL×2) and H$_2$O (110 mL×2), and dried in vacuum at 40° C. overnight.

$^1$H-NMR (500 MHz, CDCl$_3$): δ 5.45 (d, J=7.9 Hz, 1H), 4.82 (s, 1H), 3.77 (s, 3H), 3.23 (s, 3H), 2.66 (m, 2H), 2.03 (t, J=2.7 Hz, 1H), 1.44 (s, 9H). $^{13}$C-NMR (125 MHz, CDCl$_3$): δ 171.0, 155.4, 80.1, 79.1, 71.4, 61.9, 49.3, 32.4, 28.5, 22.9.

Step 2: Aryl Grignard Addition to Provide Ketone 5:
Method A:

To a nitrogen degassed, light brown solution of 2-bromo-1,4-difluorobenzene (48.3 mL, 0.429 mol) in CH$_2$Cl$_2$ (500 mL) was added i-PrMgCl (2.0 M in THF, 205 mL, 0.41 mol) slowly while the internal temperature was maintained below −15° C. The resulting reaction mixture was aged for additional 30 min. In a separate 500-mL round bottom flask, the Weinreb amide 4 (50 g, 0.195 mol) was dissolved in CH$_2$Cl$_2$ (300 mL) and cooled to −15° C. The Weinreb amide solution was transferred to the above aryl Grignard solution via cannula over 1 h such that temperature was less than −15° C. The reaction mixture was allowed to warm to room temperature upon completion of addition and aged overnight. The reaction mixture was quenched into a 3-L round bottom flask containing 1.2 L of half-saturated aqueous NH$_4$Cl via cannula. The pH of the solution was then adjusted to 7 with concentrated HCl. Upon separation of the layers, the organic layer was dried over MgSO$_4$ in preparation for isolation.

Method B:

To a solution of 1-bromo-2,5-difluorobenzene (42.2 g, 0.218 mol) in toluene (85 mL) at −10 to −5° C. was added iPrMgCl/LiCl solution (1.0 M in THF, 240 mL, 0.24 mol) dropwise over 1.5 h. The reaction solution was then aged for 30 min at −10 to −5° C.

In a separate vessel, Weinreb amide 4 (28 g, 0.109 mol) was dissolved in THF (112 mL), cooled to 15° C. and then charged to the above Grignard solution over about 30 min, while the internal temperature was maintained at −10 to −5° C. The reaction mixture was then warmed to 20° C. over 1 h, and aged for additional 1 h at 20° C. for complete reaction. The reaction mixture was quenched with an aqueous HCl solution (32.5 g of concentrated hydrochloric acid in 110 mL of water) at 0 to 10° C. over 30 min. The organic phase was washed with 10% NaCl solution (200 mL×2). The organic phase was solvent switched to iPrOH (final volume about 270 mL) and water (380 mL) was added over 1 h at 20° C. Solids were filtered and washed with 40% iPrOH in water (60 mL×2). The wet cake was dried under vacuum at 45° C.

$^1$H-NMR (500 MHz, CDCl$_3$): δ 7.56 (m, 1H), 7.25 (m, 1H); 7.15 (m, 1H), 5.67 (d, J=7.3 Hz, 1H), 5.24 (m, 1H), 2.91 (m, 1H), 2.68 (m, 1H), 2.00 (t, J=2.43, 1H), 1.45 (s, 9H). $^{13}$C-NMR (125 MHz, CDCl$_3$): δ 159.03 (dd, J=245.5, 1.8 Hz), 157.4 (d, J=248.0 Hz), 124.6 (dd, J=15.4, 6.2 Hz), 122.2 (dd, J=24.6, 9.8 Hz), 118.4 (dd, J=27.1, 8.0 Hz), 117.6 (DD, J=25.2, 3.7 Hz), 80.4, 78.4, 72.1, 57.9 (d, J=7.5 Hz), 28.5, 22.3.

Step 3: Dynamic Kinetic Resolution Reduction to Provide 6

To a nitrogen degassed solution of ketone 5 (58 g, 0.184 mol), RuCl((R,R)-pentafluorophenylsulfonyl-DPEN)(p-cymene) (654 mg, 0.919 mmol), and DABCO (61.8 g, 0.551 mol) THF (570 mL) at ambient temperature was added formic acid (35.2 mL, 0.919 mol) dropwise. The solution was warmed to 35° C. and aged for 20 h. The batch (700 mL) was concentrated to 350 mL. iPAc (350 mL) was added and the mixture was washed with 0.5 N HCl (500 mL). The organic phase was washed with saturated aqueous sodium hydrogencarbonate (350 mL) followed by water (150 mL). The final organic phase was about 670 mL, which was directly used for the next step.

Step 4: Rh-Catalyzed Cycloisomerization to Provide 7

The catalyst [tris(3-fluorophenyl)P]$_3$RhCl was prepared as follows. To an inerted reaction vessel was charged 95:5 ethanol/water (55 mL). The solution was purged with three nitrogen gas/vacuum cycles. To this solution under a nitrogen gas atmosphere was added rhodium trichloride hydrate (59 g, 0.224 mol) and tris(3-fluorophenyl)phosphine (297.6 g, 0.941 mol) and the vessel was purged with three nitrogen gas/vacuum cycles. Under a nitrogen gas atmosphere, the solution was heated at reflux temperature (78° C.) and aged 2.5 h at this temperature. The reaction mixture was then cooled to 20° C. over one hour and then filtered. The wet cake was washed with 95:5 ethanol/water (500 mL) and then dried with a stream of nitrogen for 18 h to afford the desired Rh catalyst.

A mixture of the DKR alcohols (6:10=88:12, 20.0 g by assay of combined diastereoisomers) was dissolved in 30 mL of DMF. The resulting solution was degassed with N$_2$. In a separate flask, [tris(3-fluorophenyl)P]$_3$RhCl (1.4 g, 1.28 mmol) was then charged to 110 mL of DMF. The resulting solution was degassed with N$_2$. This solution was then heated to 80° C. By use of a syringe pump, the solution of alcohols 6+10 in DMF was added to the Rh catalyst/DMF solution over 2 h. The reaction solution was stirred for additional 14 h. Upon cooling to room temperature, the reaction solution was added to a flask charged with a stirring biphasic solution comprised of 90 mL of toluene and 240 mL of 5% aqueous NaHCO$_3$ over 30 min. After 30 min of agitation, the organic phase was separated. The aqueous DMF phase was extracted with 70 mL of toluene. The combined organic phase was washed with H$_2$O (90 mL×3). 6 has two rotomers in chloroform in about a 4:1 ratio at ambient temperature. For the major rotomer of 6: $^1$H-NMR (500 MHz, CDCl$_3$): δ 7.18 (m, 1H), 6.98 (m, 2H), 6.52 (m, 1H), 5.0 (d, J=5.7 Hz, 1H), 4.78 (m, 1H), 4.72 (m, 1H), 3.98 (m, 1H), 2.22 (m, 1H), 2.01 (m, 1H), 1.34 (s, 9H). $^{13}$C-NMR (125 MHz, CDCl$_3$): δ 159.1 (dd, J=242.4, 1.8 Hz), 155.9 (d, J=241.8 Hz), 155.0, 143.5, 128.0

(dd, J=18.5, 9.2 Hz), 116.5 (dd, J=26.5, 8.6 Hz), 116.1 (24.6, 8.6 Hz), 114.9 (dd, J=25.2, 4.3 Hz), 99.1, 79.8, 74.1, 47.7, 28.4, 26.0.

Alternative Step 4: Ru-Catalyzed Cycloisomerization to Provide 7

To a solution of a mixture of DKR alcohols (6:10) (43.2 g, 0.139 mol, 88:12 ratio of the two diastereoisomers) in DMF (108 mL) was added tetrabutylammonium hexafluorophosphate (6.99 g, 18.03 mmol), N-hydroxysuccinimide (7.98 g, 69.35 mmol), NaHCO$_3$ (6.06 g, 72.1 mmol), followed immediately by CpRuCl(PPh$_3$)$_2$ (2.22 g, 3.05 mmol) and PPh$_3$ (2.4 g, 9.15 mmol) under a nitrogen atmosphere. After degassing with N$_2$, the reaction mixture was gradually warmed to 85° C. After 26 h, greater than 99% conversion was achieved. The reaction mixture was cooled to ambient temperature and the solid was filtered off. The wet cake was washed with DMF (40 mL). 5% aqueous NaHCO$_3$ (500 mL) and toluene (200 mL) were added to the filtrate. The organic phase was separated and the aqueous phase was back-extracted with toluene (100 mL). The combined organic phase was then washed with water (2×150 mL). The solution was azetropically dried and was used directly in the next step.

Step 5: Hydroboration/Oxidation to Provide 8

The toluene solution of the dihydropyran products from Step 4 (24.6 g by assay, 79.0 mmol) was transferred to a 500-mL flask, rinsing with 25 mL toluene, and then 150 mL of MTBE was added. The resulting solution was cooled to −7° C., and then BH$_3$—SMe$_2$ (18.7 mL, 0.198 mol) was added dropwise over 30 min. After aging an additional 2 h, the reaction solution was warmed gradually to 15° C. over 30 min. The reaction was then quenched by transferring to a stirred solution of 1 N NaOH (250 mL) while the temperature was maintained below 25° C. Sodium perborate tetrahydrate (36.5 g, 237 mmol) was then added in portions. After aging overnight, the organic phase was separated and washed with H$_2$O (125 mL). The organic phase was azetropically solvent-switched to toluene. The batch temperature was raised to 80° C. n-Bu$_3$P (3.95 mL, 15.8 mmol) was added and the resulting solution was aged for 1 h at 80-85° C. Heptane (148 mL) was added dropwise over 2 h. The product was collected by filtration, washed with heptane/toluene=2/1 (74 mL) and heptane (50 mL), and dried in vacuo to give the desired product as an off-white solid.

8 is a mixture of two diastereoisomers in about a 3:2 ratio. Each diastereoisomer has two rotamers in DMSO in about 4:1 ratio at ambient temperature. For the major rotomer of the major diastereoisomer 8: $^1$H-NMR (500 MHz, DMSO-d$_6$): δ 7.27 (m, 1H), 7.13 (m, 2H), 6.87 (d, J=9.6 Hz, 1H), 4.97 (d, J=3.8 Hz, 1H), 4.18 (d, J=9.9 Hz, 1H), 3.89 (m, 1H), 3.60 (m, 1H), 3.30 (s, 1H), 3.01 (t, J=10.4 Hz, 1H), 2.07 (m, 1H), 1.54 (dd, J=13.0, 6.9 Hz, 1H), 1.17 (s, 9H). For the major rotomer of the minor diastereoisomer 8: $^1$H NMR (500 MHz, DMSO-d$_6$): δ 7.13 (m, 3H), 6.74 (d, J=9.8 Hz, 1H), 4.85 (d, J=3.7 Hz, 1H), 4.27 (d, J=9.8 Hz, 1H), 3.92 (m, 1H), 3.81 (s, 1H), 3.76 (d, J=12.0 Hz, 1H), 3.48 (d, J=11.8 Hz, 1H), 1.86 (m, 1H), 1.77 (m, 1H), 1.17 (s, 9H).

$^{13}$C-NMR (100 MHz, CDCl$_3$): a mixture of two diastereoisomers in about a 3:2 ratio. δ 159.1 (m, 2C), 156.4 (m, 2C), 155.0, 154.8, 146.0 (m, 2C), 128.3 (m, 2C), 116.1 (dd, J=24.9, 8.8 Hz, 2C), 115.4 (dd, J=24.9, 4.8 Hz), 115.2 (dd, J=24.9, 4.0 Hz), 79.8, 77.1, 76.4, 72.81, 72.76, 66.0, 65.5, 51.4, 48.2, 40.6, 38.1, 28.3 (6C).

Step 6: Ru Oxidation to Provide 9

To a solution of the alcohol 8 (40.0 g, 121.4 mmol) in CH$_3$CN (120 mL), AcOH (20 mL), and H$_2$O (20 mL) was added a solution of RuCl$_3$ (50.4 mg, 0.243 mmol) in H$_2$O (40 mL) at 0° C. NaBrO$_3$ (9.2 g, 60.7 mmol) was added in portions at 0° C. The resulting reaction mixture was stirred at 0° C. until a complete consumption of alcohol 8 was achieved by HPLC. H$_2$O (600 mL) was added dropwise over 5 h at 0° C. The slurry was aged overnight at 0° C. The product was collected by filtration, washed with CH$_3$CN/H$_2$O=⅙ (200 mL×2), and dried under vacuum to give 9. 9 has two rotamers in DMSO in about a 4:1 ratio at ambient temperature. For the major rotomer of 9: $^1$H NMR (500 MHz, DMSO-d$_6$): δ 7.27 (m, 1H), 7.20 (m, 2H), 7.12 (d, J=9.2 Hz, 1H), 4.76 (d, J=9.5 Hz, 1H), 4.19 (d, J=16.1H), 4.10 (d, J=16.1 z, 1H), 4.05 (m, 1H), 2.76 (dd, J=16.4, 6.2 Hz, 1H), 2.71 (dd, J=16.4, 10.1 Hz, 1H), 1.20 (s, 9H). $^{13}$C-NMR (125 MHz, d$_6$-DMSO): δ 205.4, 158.0 (d, J=236.9 Hz), 156.2 (dd, J=241.8, 1.8 Hz), 154.2, 127.8 (dd, J=16.0, 8.0 Hz), 116.6 (dd, J=25.2, 8.0 Hz), 116.2 (dd, J=23.4, 8.0 Hz), 115.2 (dd, J=24.0, 3.1 Hz), 77.9, 74.5, 73.6, 50.6, 44.1, 27.9.

What is claimed is:

1. A process for preparing a compound of structural formula (I):

wherein Ar is phenyl optionally substituted with one to five R$^1$ substituents;

each R$^1$ is independently selected from the group consisting of:
   fluorine,
   chlorine,
   C$_{1-6}$ alkyl, optionally substituted with one to five fluorines, and
   C$_{1-6}$ alkoxy, optionally substituted with one to five fluorines;

and P represents a primary amine protecting group;

comprising the step of treating a compound of structural formula (VII) with an oxidizing agent in a suitable solvent:

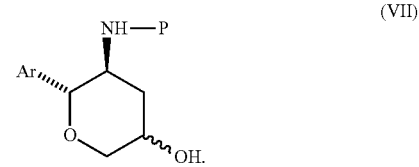

2. The process of claim 1 additionally comprising the step of producing a compound of structural formula (VII):

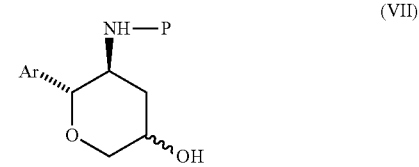

by hydroboration of a compound of structural formula (VI) with a borane reagent followed by oxidative work-up:

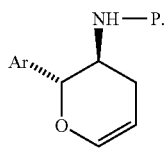

3. The process of claim 2 additionally comprising the step of producing a compound of structural formula (VI):

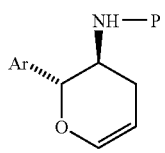

by subjecting a compound of structural formula (V):

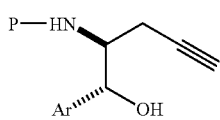

to rhodium- or ruthenium-catalyzed cycloisomerization conditions in a suitable organic solvent.

4. The process of claim 3 additionally comprising the step of producing a compound of structural formula (V):

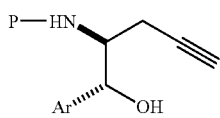

by treating a compound of structural formula (III):

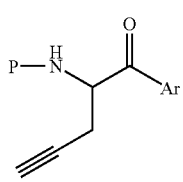

in a suitable organic solvent with a source of hydrogen, a base, and a Ru($\eta^6$-arene)-N-sulfonyl-1,2-diamine catalyst.

5. The process of claim 4 additionally comprising the step of producing a compound of structural formula (III):

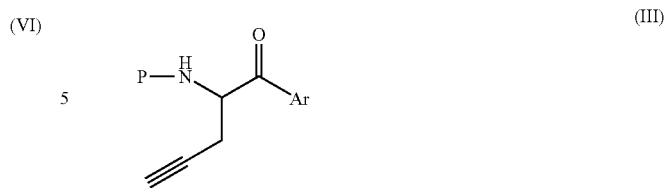

by treating a compound of structural formula (II):

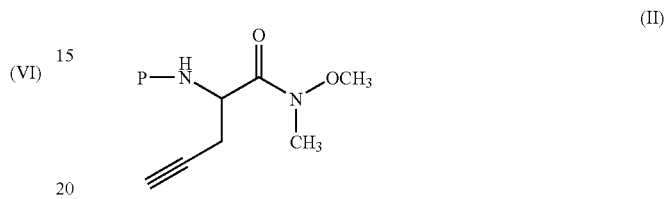

with a Grignard reagent of structural formula (IV):

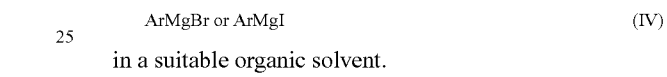

ArMgBr or ArMgI     (IV)

in a suitable organic solvent.

6. The process of claim 5 additionally comprising the step of producing a compound of structural formula (II):

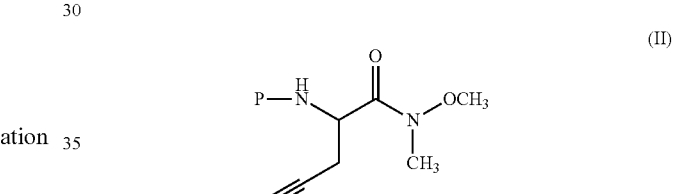

by (i) alkylating a $C_{1-6}$ alkyl N-(diphenylmethylene)glycinate with a propargyl sulfonate or propargyl halide in the presence of base followed by treatment with acid to liberate the free primary amine; (ii) reacting said liberated primary amine with a primary amine protecting reagent in the presence of base; and (iii) treating the resulting N-protected amino acid with N,O-dimethylhydroxylamine in the presence of an activating reagent in a suitable organic solvent.

7. The process of claim 6 additionally comprising the step of isolating the compound of structural formula (I).

8. The process of claim 1 wherein Ar is 2,5-difluorophenyl or 2,4,5-trifluorophenyl.

9. The process of claim 1 wherein P is t-butyloxycarbonyl.

10. The process of claim 9 wherein Ar is 2,5-difluorophenyl.

11. A process for preparing a compound of structural formula (VIII):

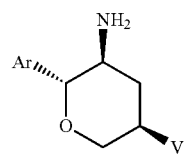

wherein V is selected from the group consisting of:

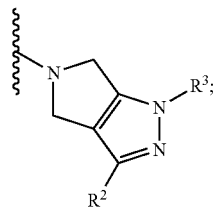 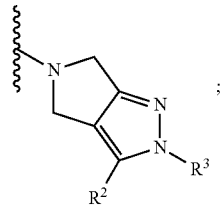

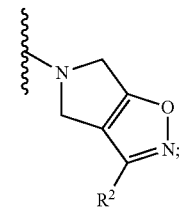 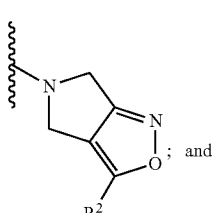

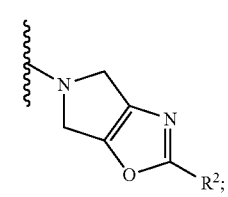

and $R^2$ and $R^3$ are each independent selected from the group consisting of hydrogen, $C_{1-3}$ alkyl, trifluoromethyl, 2,2,2-trifluoroethyl, and cyclopropyl;

comprising the steps of:

(a) producing a compound of structural formula (II):

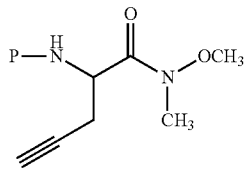

(II)

by (i) alkylating a $C_{1-6}$ alkyl N-(diphenylmethylene)glycinate with a propargyl sulfonate or propargyl halide in the presence of base followed by treatment with acid to liberate the free primary amine; (ii) reacting said liberated primary amine with a primary amine protecting reagent in the presence of base; and (iii) treating the resulting N-protected amino acid with N,O-dimethylhydroxylamine in the presence of an activating reagent in a suitable organic solvent;

(b) producing a compound of structural formula (III):

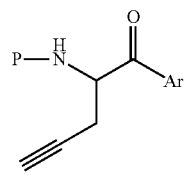

(III)

by treating a compound of structural formula (II) with a Grignard reagent of structural formula (IV):

ArMgBr or ArMgI (IV)

in a suitable organic solvent;

(c) producing a compound of structural formula (V):

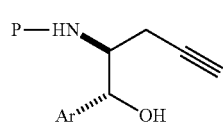

(V)

by treating a compound of structural formula (III) in a suitable organic solvent with a source of hydrogen, a base, and a Ru($\eta^6$-arene)-N-sulfonyl-1,2-diamine catalyst;

(d) producing a compound of structural formula (VI):

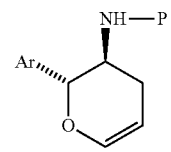

(VI)

by subjecting a compound of structural formula (V) to rhodium- or ruthenium-catalyzed cycloisomerization conditions in a suitable organic solvent;

(e) producing a compound of structural formula (VII):

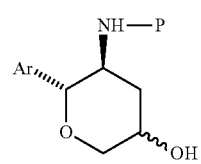

(VII)

by hydroboration of a compound of structural formula (VI) with a suitable borane reagent followed by oxidative work-up;

(f) treating a compound of structural formula (VII) with a suitable oxidizing agent in a suitable solvent to afford a compound of structural formula (I):

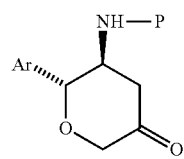

(I)

wherein Ar is phenyl optionally substituted with one to five $R^1$ substituents;

each $R^1$ is independently selected from the group consisting of:
fluorine,
chlorine,
$C_{1-6}$ alkyl, optionally substituted with one to five fluorines, and
$C_{1-6}$ alkoxy, optionally substituted with one to five fluorines;

and P represents a primary amine protecting group; and (g) converting the compound of structural formula (I) into a compound of structural formula (VIII).

12. The process of claim 11 wherein Ar is 2,5-difluorophenyl.

* * * * *